US00PP12515P2

(12) United States Plant Patent
Vandenberg et al.

(10) Patent No.: US PP12,515 P2
(45) Date of Patent: Apr. 2, 2002

(54) CHRYSANTHEMUM PLANT NAMED 'YOSEATTLE'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,750

(22) Filed: Jun. 16, 2000

(51) Int. Cl.[7] ..... A01H 5/00
(52) U.S. Cl. ..... Plt./298
(58) Field of Search ..... Plt./298

(56) References Cited

U.S. PATENT DOCUMENTS

PP5,721 P * 4/1986 Hesse ..... Plt./298
PP6,586 P * 2/1989 VandenBerg ..... Plt./298
PP9,914 P * 6/1997 Rabb ..... Plt./298
PP10,571 P * 8/1998 VandenBerg ..... Plt./298

OTHER PUBLICATIONS

UPOV–ROM, 2001/03, Plant Variety Database, GTI Jouve Retrieval Software, citation for 'Yoseattle'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yoseattle', characterized by its upright and uniformly mounded plant habit; vigorous growth habit; uniform flowering response; early flowering, eight-week response time; floriferousness; daisy-type inflorescences that are about 7.5 cm in diameter; intense red-colored ray florets that do not fade; green disc florets develop slowly maintaining green coloration; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yoseattle.

The new Chrysanthemum is a product of a planned breeding program conducted by the Inventors in Salinas, Calif. and Fort Myers, Fla. The objective of the breeding program is to create new potted Chrysanthemum cultivars with desirable inflorescence form and floret colors and good postproduction longevity.

The new Chrysanthemum originated from a cross made by the Inventors in May, 1993, in Salinas, Calif., of a proprietary Chrysanthemum seedling selection identified as YB-4196 as the female, or seed, parent with a proprietary Chrysanthemum seedling selection identified as YB-6496, as the male, or pollen, parent. The new Chrysanthemum was discovered and selected by the Inventors in December, 1996, as a single flowering plant within the progeny of the stated cross grown in a controlled environment in Fort Myers, Fla. The selection of this plant was based on its desirable inflorescence form and floret colors and good postproduction longevity.

Asexual reproduction of the new Chrysanthemum by vegetative tip cuttings was first conducted in Fort Myers, Fla. in February, 1997. Asexual reproduction by cuttings has shown that the unique features of this new Chrysanthemum are stable and reproduced true to type in successive generations.

SUMMARY OF THE INVENTION

The cultivar Yoseattle has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoseattle'. These characteristics in combination distinguish 'Yoseattle' as a new and distinct Chrysanthemum:

1. Upright and uniformly mounded plant habit.
2. Vigorous growth habit.
3. Uniform flowering response.
4. Early flowering, eight-week response time.
5. Freely flowering.
6. Daisy-type inflorescences that are about 7.5 cm in diameter.
8. Intense red-colored ray florets that do not fade. Green disc florets develop slowly maintaining green coloration.
9. Can be grown as a natural spray-type.
10. Good postproduction longevity with inflorescences maintaining good substance and color for about three weeks in an interior environment.

Plants of the new Chrysanthemum differ from plants of the Chrysanthemum cultivar, Rage, disclosed in U.S. Plant Pat. No. 8,770, in the following characteristics:

1. Plants of the new Chrysanthemum are more outwardly spreading than plants of the cultivar Rage.
2. Plants of the new Chrysanthemum have larger inflorescences than plants of the cultivar Rage.
3. Disc floret color of the new Chrysanthemum maintains green coloration longer than disc florets of the cultivar Rage.
4. Plants of the new Chrysanthemum flower about two or three days earlier than plants of the cultivar Rage.

BRIEF DESCRIPTION OF THE PHOTOGRAPHS

The accompanying colored photographs illustrate the overall appearance of the new Chrysanthemum showing the colors as true as it is reasonably posible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yoseattle'.

The photograph at the bottom of the sheet comprises a close-up view of typical inflorescences of the cultivar Yoseattle.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yoseattle.

Commercial classification: Daisy-type potted Chrysanthemum.

Parentage:

*Female, or seed, parent.*—Proprietary Chrysanthemum seedling selection identified as YB-4196.

*Male, or pollen, parent.*—Proprietary Chrysanthemum seedling selection identified as YB-6496.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy-type potted Chrysanthemum which can be grown as a natural spray-type. Inverted triangle; stems mostly upright and somewhat outwardly spreading giving a uniformly mounded appearance to the plant. Freely branching, about four lateral branches develop after removal of terminal apex (pinching); dense and full plants. Vigorous.

*Plant height.*—About 30 cm.

*Plant width.*—About 35 cm.

*Lateral branches.*—Length: About 22 cm. Diameter: About 3 mm. Internode length: About 1.8 cm. Strength: Moderately strong, flexible. Texture: Pubescent. Color: 144A.

*Foliage description.*—Arrangement: Alternate. Length: About 4.6 cm. Width: About 4.2 cm. Apex: Mucronate. Base: Mostly truncate. Margin: Palmately lobed, sinuses between lateral lobes mostly convergent, occasionally overlapping. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147A to 147B. Venation lower surface: 147B. Petiole length: About 2.3 cm. Petiole diameter: About 2.5 mm. Petiole color: 147A and 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Typically grown as a spray-type; about six inflorescences per lateral stem, about 24 inflorescences per plant.

*Inflorescence bud.*—Height: About 6 mm. Diameter: About 7 mm. Color: Close to 143A.

*Inflorescence size: Diameter: About* 7.5 cm. Depth (height): About 1.6 cm. Diameter of disc: About 1.75 cm. Receptacle diameter: About 6.5 mm.

*Ray florets.*—Shape: Elongated-oblong. Orientation: Slightly upright, about 10 to 20° from perpendicular to peduncle or horizontal. Aspect: Straight and flat. Length: About 3.4 cm. Width: About 1.1 cm. Apex: Mostly acute. Base: Attenuate; short corolla tube. Margin: Entire. Texture: Smooth, glabrous, satiny. Number of ray florets per inflorescence: About 24; one or two rows. Color: When opening, upper surface: 53A to darker and more intense than 46A. When opening, lower surface: 53A. Fully opened, upper surface: More intense and slightly darker than 45A to 46A. Fully opened, lower surface: More red than 181A.

*Disc florets.*—Shape: Tubular, elongated. Apex: Five-pointed. Length: About 6.5 mm. Width: Apex, about 1.5 mm; base, about 1 mm. Number of disc florets per inflorescence: About 127. Color: Immature: 144A; development occurs slowly and green color is maintained. Mature: Apex: 9A. Mid-section: Close to 154C to 154D. Base: 155D.

*Peduncles.*—Length: First peduncle: About 6.5 cm. Fourth peduncle: About 9.3 cm. Diameter: About 3 mm. Angle to vertical: About 40 to 45° from vertical. Strength: Moderately strong, flexible. Color: 144A.

*Reproductive organs.*—Androecium: Present on disc florets only. Anther color: 9A. Pollen amount: Moderate. Pollen color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yoseattle', as illustrated and described.

* * * * *

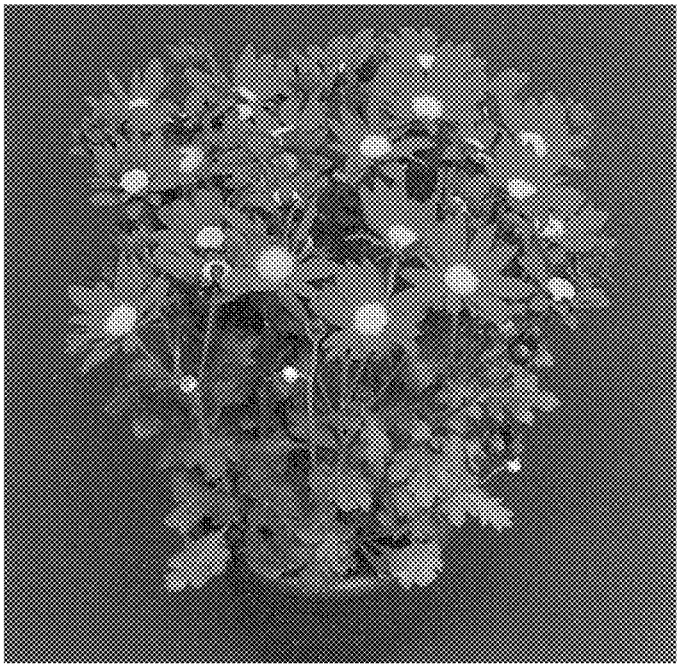
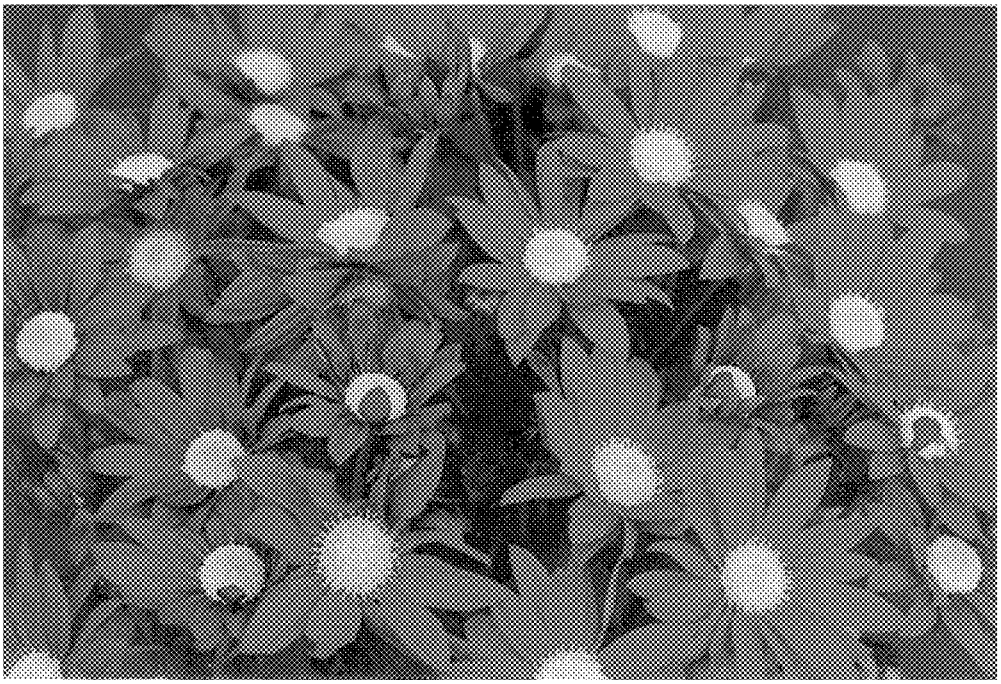

UNITED STATES PATENT AND TRADEMARK OFFICE

CERTIFICATE OF CORRECTION

PATENT NO. : PP 12,515 P2
DATED : April 2, 2002
INVENTOR(S) : Vandenberg et al.

It is certified that error appears in the above-identified patent and that said Letters Patent is hereby corrected as shown below:

Title page,
Item [*] Notice, delete the phrase "by 0 days" and insert -- by 20 days --

Signed and Sealed this

Eighteenth Day of May, 2004

JON W. DUDAS
*Acting Director of the United States Patent and Trademark Office*